United States Patent
Le Gars et al.

(10) Patent No.: US 6,905,666 B2
(45) Date of Patent: Jun. 14, 2005

(54) PROCESS FOR THE SELECTIVE DECOMPOSITION OF HYDRAZINE IN A HYDRAZINE/SUBSTITUTED HYDRAZINE/ WATER MIXTURE

(75) Inventors: Pierre Le Gars, Toulouse (FR); Denis Souyri, Toulouse (FR); Henri Delalu, Lyons (FR); Jacques Berthet, Lyons (FR)

(73) Assignee: Isochem, Paris (FR)

( * ) Notice: Subject to any disclaimer, the term of this patent is extended or adjusted under 35 U.S.C. 154(b) by 253 days.

(21) Appl. No.: 10/293,700

(22) Filed: Nov. 14, 2002

(65) Prior Publication Data

US 2003/0113260 A1 Jun. 19, 2003

(30) Foreign Application Priority Data

Dec. 14, 2001 (FR) .......................................... 01 16217

(51) Int. Cl.[7] .......................... C01B 21/02; C01B 3/04; C01C 1/02
(52) U.S. Cl. ..................... 423/351; 423/352; 423/658.2
(58) Field of Search .......................... 423/658.2, 648.1, 423/351, 352, 358

(56) References Cited

U.S. PATENT DOCUMENTS

| | | | | |
|---|---|---|---|---|
| 2,925,709 A | * | 2/1960 | Mantell et al. ............. 252/374 |
| 2,926,144 A | * | 2/1960 | Mantell et al. ............. 502/331 |
| 3,165,382 A | * | 1/1965 | Forte ....................... 423/658.2 |
| 3,931,395 A | * | 1/1976 | Beckert et al. ........... 423/648.1 |
| 4,122,671 A | | 10/1978 | Armstrong et al. |
| 4,124,538 A | | 11/1978 | Armstrong et al. |
| 4,157,270 A | * | 6/1979 | Martignoni et al. ..... 149/109.6 |
| 4,620,415 A | | 11/1986 | Schmidt |
| 4,804,527 A | | 2/1989 | Tatarchuk et al. |

FOREIGN PATENT DOCUMENTS

| | | |
|---|---|---|
| FR | 2 383 916 | 10/1978 |
| GB | 1183079 | * 3/1970 |

OTHER PUBLICATIONS

Schmidt, "Hydrazine and its derivatives", A Wiley-Interscience Publication, John Wiley & Sons, pp. 604–607, no date.

* cited by examiner

Primary Examiner—Wayne A. Langel
(74) Attorney, Agent, or Firm—Oliff & Berridge, PLC

(57) ABSTRACT

The present invention relates to a process for the selective decomposition of hydrazine in a hydrazine/substituted hydrazine/water mixture. A catalyst chosen from the group consisting of nickel supported on silica/alumina, the nickel-nickel oxide mixture supported on silica/alumina and rhodium supported on carbon is introduced into this mixture and then the mixture is heated at a temperature of between 60° C. and 120° C.

9 Claims, No Drawings

PROCESS FOR THE SELECTIVE DECOMPOSITION OF HYDRAZINE IN A HYDRAZINE/SUBSTITUTED HYDRAZINE/WATER MIXTURE

The present invention relates to a process for the selective decomposition of hydrazine in a hydrazine/substituted hydrazine/water mixture. Substituted hydrazines are compounds of use in agrochemistry, such as, for example, hexahydropyridazine, in pharmaceuticals, such as N-aminopiperidine, or for plant-protection products, such as monomethylhydrazine. In all these applications, the substituted hydrazine can be in the form of an aqueous solution but it is absolutely essential for the aqueous solution to be devoid of hydrazine.

One of the most well-known synthetic routes for preparing a substituted hydrazine, monomethylhydrazine, is the Raschig process. This consists in reacting, in a first step, ammonia with sodium hypochlorite, to form chloramine, which compound is subsequently reacted with methylamine to form monomethylhydrazine. The reaction scheme of the Raschig process is as follows:

The disadvantage of such a synthesis is the formation of hydrazine as by-product. It is therefore necessary to subsequently separate the hydrazine from the monomethylhydrazine. Such separating operations are generally expensive.

Another solution for obtaining a hydrazine-free aqueous substituted hydrazine solution is to decompose the hydrazine in the hydrazine/substituted hydrazine/water mixture.

A person skilled in the art already knows processes for the decomposition of hydrazine. Thus, U.S. Pat. No. 4,124,538 discloses a catalyst capable of decomposing hydrazine. This catalyst is composed of a metal which is iridium or an iridium/ruthenium mixture deposited on alumina. This catalyst can also be used to decompose monomethylhydrazine. It is therefore not a question here of selective decomposition. It is the same for the catalyst disclosed in U.S. Pat. No. 4,122,671. This catalyst is composed of a porous support and of a mixture of ruthenium with a metal chosen from iridium and platinum. The porous support can, for example, be composed of alumina or of silica. Such a catalyst just as easily decomposes hydrazine as monomethylhydrazine.

A person skilled in the art thus currently does not know of a process which makes it possible to selectively decompose hydrazine in a hydrazine/substituted hydrazine/water mixture, that is to say of a process in which the rate of decomposition of hydrazine is markedly greater than the rate of decomposition of the substituted hydrazine. Such a process is a subject-matter of the present invention.

The invention relates to a process for the selective decomposition of hydrazine in a hydrazine/substituted hydrazine/water mixture, characterized in that a catalyst chosen from the group consisting of nickel supported on silica/alumina, the nickel-nickel oxide mixture supported on silica/alumina and rhodium supported on carbon is introduced into the mixture and then in that the mixture is heated at a temperature of between 60° C. and 120° C.

This process makes it possible to selectively decompose hydrazine with respect to the substituted hydrazine. This is because, on introducing the catalyst described above into a hydrazine/substituted hydrazine/water mixture, 95% of the hydrazine is decomposed against only 10% of substituted hydrazine. The catalyst comprises from 0.5% to 70% by weight of metal element with respect to the total weight of the catalyst. The term "metal element" refers to the metal in the form of oxide and of metal.

The catalyst preferably comprises from 45% to 70% by weight of metal element with respect to the total weight of the catalyst.

A preferred catalyst is the nickel-nickel oxide mixture supported on silica/alumina.

The substituted hydrazine is a hydrazine of formula (I)

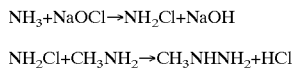

in which:
R$^1$ and R$^3$ represent a hydrogen atom or a substituted or unsubstituted and linear or branched C$_1$–C$_6$ alkyl group,
R$^2$ represents a substituted or unsubstituted and linear or branched C$_1$–C$_6$ alkyl group,
it being possible for R$^1$ and R$^2$ together to form, with the nitrogen atom to which they are bonded, a heterocycle, and
it being possible for R$^2$ and R$^3$, when R$^1$ represents a hydrogen atom, together to form, with the two nitrogen atoms, a heterocycle.

The substituents of R$^1$, R$^2$ and R$^3$, when R$^1$, R$^2$ and R$^3$ represent a C$_1$–C$_6$ alkyl group, are independently a halogen atom, a carboxyl group or a nitrile group.

The substituted hydrazine can thus be substituted by one alkyl group only. R$^1$ and R$^3$ then each represent a hydrogen atom and R$^2$ represents a linear or branched alkyl group. Mention may in particular be made of monomethylhydrazine, isopropylhydrazine and isobutylhydrazine.

The substituted hydrazine can also be an exocyclic hydrazine, R$^1$ and R$^2$ forming, with the nitrogen atom to which they are bonded, a heterocycle; this is the case for N-aminopiperidine.

Finally, the substituted hydrazine can be an endocyclic hydrazine, R$^2$ and R$^3$ forming, together with the two nitrogen atoms, a heterocycle and R$^1$ representing a hydrogen atom; this is the case of hexahydropyridazine.

The substituted hydrazine is preferably in excess or in equimolar proportion with respect to hydrazine in the hydrazine/substituted hydrazine/water mixture. The content by weight of water is between 10% and 90% by weight with respect to the total weight of the mixture.

A preferred embodiment of the invention is now given. The hydrazine/substituted hydrazine/water mixture is introduced into a reactor which does not influence the reaction. The reactor used is a glass or PTFE reactor.

The hydrazine/substituted hydrazine/water mixture comprises from 0.01 to 1 mol of hydrazine with respect to the substituted hydrazine. The preferred substituted hydrazines are monomethylhydrazine, isopropylhydrazine, isobutylhydrazine, hexahydropyridazine and N-aminopiperidine.

The catalyst, chosen from the group consisting of nickel on silica/alumina, the nickel-nickel oxide mixture on silica/alumina and rhodium on carbon, is introduced into the same reactor.

A preferred catalyst is the nickel-nickel oxide mixture supported by the silica/alumina mixture.

The total amount of the metal element used for the catalyst is between 0.5% and 70% by weight with respect to the total weight of the catalyst and preferably between 45% and 70%.

The reaction medium is subsequently heated at a temperature of between 60° C. and 120° C., preferably between 80° C. and 90° C. It will be seen to that the pressure inside the reactor is approximately 1 bar. Higher pressures can be used.

The reaction medium is stirred throughout the duration of the heating.

The heating time is between 0.5 hour and 8 hours and it depends on the catalyst used. Thus, on using the nickel-nickel oxide supported on silica/alumina catalyst, it is sufficient to heat for 3 hours, whereas, when the rhodium supported on carbon catalyst is used, it is necessary to heat for 7 hours.

After heating, and when the temperature of the reaction medium is ambient temperature, the catalyst is recovered by filtration under an inert atmosphere, preferably under nitrogen.

The solution obtained is analysed by gas chromatography. It comprises less than 0.01% by weight of hydrazine with respect to the substituted hydrazine.

The examples which follow illustrate, without implied limitation, possible ways of implementing the invention.

EXAMPLE 1

Nickel-Nickel Oxide on Silica/Alumina Catalyst 200 ml of a solution containing 40% by weight of monomethylhydrazine, 4% by weight of hydrazine and 56% by weight of water are introduced into a 500 ml reactor.

0.25 g of nickel-nickel oxide supported by a silica/alumina mixture catalyst is introduced into this same reactor. The catalyst comprises 31% by weight of nickel and 32% by weight of nickel oxide, i.e. 56% by weight of nickel element, with respect to the total weight of the catalyst.

The medium is subsequently heated at 88° C. for 3 hours while being stirred.

After heating and when the temperature of the medium had been brought back to ambient temperature, the catalyst is recovered by filtration under nitrogen and the medium is analysed by gas chromatography. The following composition is obtained: 39% by weight of monomethylhydrazine, 0.1% of hydrazine and 60.9% of water.

EXAMPLE 2

Rhodium on Carbon Catalyst

The same procedure is followed as that described in Example 1, except for the heating time.

The starting composition is also identical to that of Example 1.

The catalyst comprises 5% by weight of rhodium with respect to the total weight of the catalyst.

Heating time: 7 hours

Final composition: 38% monomethylhydrazine
0.05% hydrazine
61.95% water.

COMPARATIVE EXAMPLES 3–5

These examples do not form part of the invention. They were carried out for the purpose of showing that the fact of using nickel-nickel oxide or nickel on silica/alumina or rhodium on carbon catalysts does not correspond to an arbitrary choice but corresponds to a selection necessary in order to obtain the desired technical effect.

COMPARATIVE EXAMPLES 3 AND 4

Tests were carried out with catalysts based on ruthenium and on iridium supported on carbon (Ru/C and Ir/C) under the same operating conditions as those described in Example 1. The decomposition of hydrazine and of the substituted hydrazine is extremely slow, of the order of several days, and no selectivity is observed.

COMPARATIVE EXAMPLE 5

The same test was carried out with Raney nickel (48% by weight of nickel and 52% by weight of aluminium). The decomposition of hydrazine and of the substituted hydrazine is fast (of the order of 30 minutes) but no selectivity is observed.

What is claimed is:

1. Process for the selective decomposition of hydrazine in a hydrazine/substituted hydrazine/water mixture, wherein a catalyst chosen from the group consisting of nickel supported on silica/alumina a nickel—nickel oxide mixture supported on silica/alumina, and rhodium supported on carbon is introduced into the mixture and then the mixture is heated at a temperature of between 60° C. and 120° C.

2. Process according to claim 1, wherein the catalyst comprises from 0.5% to 70% by weight of metal element with respect to the total weight of the catalyst.

3. Process according to claim 2, wherein the catalyst comprises from 45% to 70% by weight of metal element with respect to the total weight of the catalyst.

4. Process according to claim 1, wherein the substituted hydrazine is a hydrazine of formula (I)

in which:
R$^1$ and R$^3$ represent a hydrogen atom or a substituted or unsubstituted and linear or branched C$_1$–C$_6$ alkyl group,
R$^2$ represents a substituted or unsubstituted and linear or branched C$_1$–C$_6$ alkyl group,
it being possible for R$^1$ and R$^2$ together to form, with the nitrogen atom to which they are bonded, a heterocycle, and
it being possible for R$^2$ and R$^3$, when R$^1$ represents a hydrogen atom, together to form, with the two nitrogen atoms, a heterocycle.

5. Process according to claim 4, wherein R$^1$ and R$^3$ represent a hydrogen atom and R$^2$ represents the methyl group.

6. Process according to claim 1, wherein the catalyst is the nickel—nickel oxide mixture supported on silica/alumina.

7. Process according to claim 1, wherein the reaction mixture is heated at a temperature of between 80° C. and 90° C.

8. Process according to claim 1, wherein the amount of hydrazine is between 0.01 mol and 1 mol per mole of substituted hydrazine.

9. Process according to claim 1, wherein the content of water in the hydrazine/substituted hydrazine/water mixture is between 10% and 90% by weight with respect to the total weight of the mixture.

* * * * *